United States Patent [19]

Messina et al.

[11] Patent Number: 4,945,161
[45] Date of Patent: Jul. 31, 1990

[54] PROCESS FOR THE PREPARATION OF N,N'-BIS-(2-HYDROXY-ETHYL) PIPERAZINE

[75] Inventors: Giuseppe Messina, Alghero; Paolo Calaresu, Sassari; Loreno Lorenzoni, Porto Torres, all of Italy

[73] Assignee: Enichem Anic S.p.A., Palermo, Italy

[21] Appl. No.: 345,361

[22] Filed: Apr. 21, 1989

[30] Foreign Application Priority Data

Apr. 21, 1988 [IT] Italy ................. 20273 A/88

[51] Int. Cl.$^5$ ........................... C07D 295/08
[52] U.S. Cl. ................................... 544/401
[58] Field of Search ......................... 544/401

[56] References Cited

U.S. PATENT DOCUMENTS 3,845,059 10/1974 Beale, Jr. ........................ 544/401

FOREIGN PATENT DOCUMENTS 249958 10/1987 Japan .

OTHER PUBLICATIONS

Paul et al., Chem. Abst. 80-10500d (1974).
Goupil, Chem. Abst. 87-201585q (1977), eq. DE-2706826.
Sasagawa et al., Chem. Abst. 87-6019f (1977), JP 76,141,895.
Schlicht, Chem. Abst. 94-106223f (1981), U.S. Pat. No. 4,235,730.
Thorel, Chem. Abst. 95-175822h (1981), BE-888,136.
Chenevert et al., Chem. Abst. 100-6485s (1984).
Buoeen et al., Chem. Abst. 102-166722m (1985).
Enichem Anic S.p.A., Chem. Abst. 109-92287u (1988), JP-621249,958 (eq. EP 245631 cited on Spec. p. 6).
Gardner et al., JACS, vol. 55, p. 3823 (1933).

*Primary Examiner*—Cecilia Shen
*Attorney, Agent, or Firm*—Oblon, Spivak, McClelland, Maier & Neustadt

[57] ABSTRACT

A new process for preparing N,N'-bis-(2-hydroxyethyl)-piperazine (I)

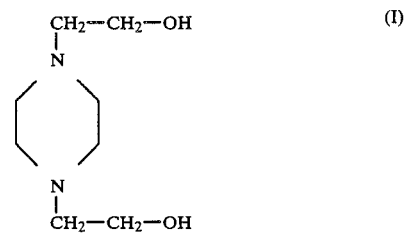

is described which involves reaction of oxamide with excess diethanolamine at a temperature of from 50° to 268° C.

10 Claims, No Drawings

PROCESS FOR THE PREPARATION OF N,N'-BIS-(2-HYDROXY-ETHYL) PIPERAZINE

The present invention refers to a new process for preparing N,N'-bis-(2-hydroxyethyl)-piperazine (I)

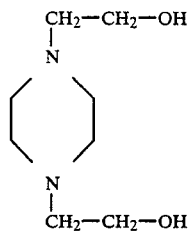

starting from oxamide (II)

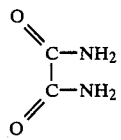

and diethanolamine (III)

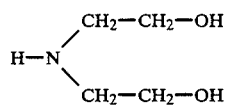

N,N'-bis-(2-hydroxyethyl)-piperazine, usually indicated as "diethanolpiperazine", is a chemical compound of remarkable interest mainly as an intermediate in the pharmaceutical industry (cfr. BE No. 888139; DE No. 2706826; Chem. Abst. 89 : 173626, 80 : 10500), in the polymer industry (Chem. Abst. 102 : 166722, 100 : 6485) and in the lubricant industry (U.S. Pat. No. 4235730).

The classical method of synthesis of this compound, reported in J.Am. Chem. Soc., 55, 3823 (1933), involves condensation of piperazine with 2-chloroethanol. More recently, a different synthesis has been described which involves reaction of diethanolamine with urea or with urea pyrolysis products (see U.S. Pat. No. 3,845,059). The yields which may be obtained with this last method, calculated on the starting diethanolamine, are however low, ranging from 15 and 25%.

Finally, Japanese patent application publication No. 76,141895 (Chem. Abst. 87, 6019f), which covers the preparation of 1,4-diazabicyclo-[2.2.2]octane, describes the intermediate use of a mixture of products containing N,N'-(2-hydroxyethyl)-piperazine, obtained by heating diethanolamine with a carboxylic acid, e.g. acetic acid, and removing the water which forms.

This last process has the remarkable disadvantage of affording mixtures of different products, and the yields in N,N'-(2-hydroxyethyl)-piperazine, calculated on the starting diethanolamine, are about 25%.

It has now been found that by reacting diethanolamine with oxamide in suitably selected conditions, diethanolpiperazine, according to the following stechiometry

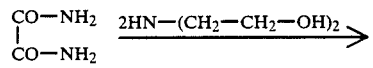

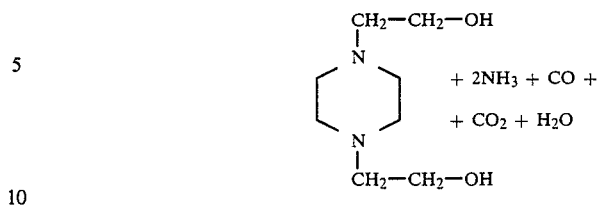

can be obtained in much higher yields.

More particularly the reaction of the present invention comprises heating a mixture of oxamide and diethanolamine, wherein the molar ratio between diethanolamine and oxamide is higher than 2, at temperatures of from 50° to 268° C. (diethanolamine boiling temperature).

The reaction may be carried out in a single step or in two separate steps. When the reaction is carried out in a single step, the mixture of oxamide and diethanolamine is heated, optionally in the presence of an inert organic solvent, at a temperature of from 130° to 268° C.

The steam which gradually forms is distilled off and the gases also are removed from the reaction environment as soon as they evolve, possibly by means of an inert gas, typically nitrogen.

The reaction yields increase with the molar ratio diethanolamine:oxamide up to a ratio of 4:1. A strong excess diethanolamine with respect to the starting oxamide may also be employed, but ratios higher than 4:1 do not afford any further improvements in yields.

A preferred molar ratio is therefore from about 2.5 to about 20, and an even more preferred molar ratio is from about 3.5 to about 10.

Preferably the temperature at which the single step process is performed ranges from 160° to 220° C. The reaction, which according to a preferred embodiment is carried out in the presence of excess diethanolamine as the reaction solvent, may also be carried out in the presence of an additional organic solvent. In this case, suitable solvents are polar and aprotic organic solvents such as polyglycols, etherated polyglycols, halogenated aliphatic or aromatic hydrocarbons, etc. Preferably said solvent is a high boiling one and more preferably it has a boiling point higher than the reaction temperature. It will therefore be possible to carry out the reaction under atmospheric pressure, so that removal of the gaseous products of the reaction can more easily be accomplished.

At the end of the reaction, the desired product is precipitated from the reaction mixture by the addition of a suitable precipitation solvent, which is conveniently selected from the class of aliphatic ketones, e.g. methyl isobutyl ketone, methyl ethyl ketone, and, preferably, acetone. The precipitate is then recovered, simply by filtration, and, if desired, it may be further purified by crystallization, while the filtrate, once the precipitation solvent has been distilled off, can directly be recycled, by reacting it with a further amount of diethanolamine.

Alternatively, the reaction may also be carried out in two separate steps; in the former step oxamide is contacted with an at least double molar amount of diethanolamine at a temperature of from 50° to 160° C., until evolution of NH3 subsides. Then diethanolamine may optionally be added to keep the molar ratio between diethanolamine and oxamide within the selected range, and the reaction temperature is brought to a value of from 160° to 268° C., and, preferably, from 160° to 220° C. During this latter step, the desired product forms with evolution of CO, $CO_2$, and $H_2O$ which are removed from the reaction environment as described before. Once gas evolution subsides, the product is recovered as described above for the single step method.

Addition of diethanolamine in the latter step is necessary when in the former step the stoichiometric amount thereof has been employed (i.e. 2 moles of diethanolamine per mole of oxamide).

Also when the reaction is carried out in two separate steps, preferably, excess diethanolamine, acting as the reaction solvent, is employed already in the former step, while the latter step is initiated by merely raising the reaction temperature.

If desired, when the reaction is carried out in two separate steps, the intermediate mixture can be isolated and separately heated, in the presence of diethanolamine, as provided for by the latter step described above.

Among the intermediate compounds which are obtained in the former step of the two step process, there is also N,N'-tetra-(2-hydroxyethyl)oxamide of formula (IV)

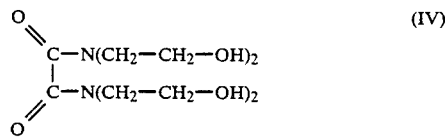

the synthesis of which, starting from oxamide and diethanolamine, has been described in EP-A-No. 245631. Simply heating this last compound, however, does not afford diethanol-piperazine. Thermal degradation products are instead obtained as well as evolution of gaseous products including $H_2O$ and $CO_2$.

On the contrary, by heating the compound of formula (IV) in the presence of diethanolamine, the desired compound of formula (I) is obtained. In this case optimum results are obtained by heating the compound of formula (IV) in the presence of at least an equimolar amount of diethanolamine with respect to the starting oxamide derivative.

A further object of the present invention is therefore a process for preparing diethanolpiperazine which comprises heating N,N'-tetra-(2-hydroxyethyl)-oxamide at temperatures of from 160° to 268° C., and, preferably, from 160° to 220° C., in the presence of diethanolamine.

The following examples which describe in detail the process of the present invention in some representative embodiments thereof, must not be interpreted as a limitation to the scopes thereof.

EXAMPLE 1

Oxamide (11.09 g, 0.126 mol) and diethanolamine (53.02 g, 0.505 mol) are charged into a 100-ml, three-necked flask, equipped with a thermometer, a water condenser, a Dean-Stark apparatus for water removal and a magnetic stirrer. The water condenser is connected to two traps, one containing 1N HCl (400 ml) and the other containing 1N NaOH (400 ml), to absorb ammonia and carbon dioxide respectively. The reaction mixture is heated at 160° C. and maintained at this temperature for one hour under a slow nitrogen stream (oxamide completely dissolves into the reaction medium and ammonia evolution is observed).

The temperature is then brought to 205° C. and, at the end of the reaction, after 23 hours altogheter, about 2.3 g of $H_2O$ are collected in the Dean-Stark apparatus and 3.86 g (0.227 mol) of ammonia and 4.93 g (0.112 mol) of carbon dioxide (as determined by titrimetry) are collected in the traps. Acetone (150 ml) is then added to the reaction mixture, the precipitate which forms is recovered by filtration and recrystallized from acetone affording 18.03 g (0.104 mol) of N,N'-bis-(2-hydroxyethyl)piperazine, corresponding to 41.04% yield, calculated on the starting diethanolamine.

EXAMPLE 2

Oxamide (10.05 g, 0.114 mol) and diethanolamine (60.43 g, 0.576 mol) are charged in a reaction flask equipped as described in Example 1.

The temperature is brought to 160° C., and the reaction mixture is maintained at this temperature, under a gentle nitrogen stream, for one hour (oxamide completely dissolves and ammonia evolves, but no carbon dioxide evolution is observed). The temperature is then brought to 205° C. and after three hours at this temperature, a sample of the evolving gas is collected with a glass gas pipet. The composition of said gas sample, by volume, is as follows $N_2=38.4\%$; $CO_2=54.59\%$; $CO=2.18\%$.

At the end of the reaction, after 23 hours altogether, acetone (150 ml) is added to the liquid left in the reaction flask (53.34 g), the precipitate is recovered and recrystallized from acetone yielding N,N'-bis-(2-hydroxyethyl)-piperazine (19.57 g, 0.112 mol, corresponding to 39.1%, calculated on the starting diethanolamine.

EXAMPLE 3

Oxamide (21.1 g, 0.24 mol) and diethanolamime (150.0 g, 1.43 mol) are charged into a 250-ml, three-necked flask, equipped with a thermometer, a water condenser, a Dean-Stark apparatus for water removal and a magnetic stirrer. The water condenser is connected to two traps, one containing 1N HCl (600 ml) and the other containing 1N NaOH (600 ml), to absorb ammonia and carbon dioxide respectively. The reaction mixture is heated to 160° C., under a gentle nitrogen stream, for one hour (while oxamide completely dissolves into the reaction mixture and evolution of ammonia and not of carbon dioxide is observed). Then the temperature is brought to 205° C. and after 1.5 hours, a sample of the evolving gas is collected, the composition of which, by volume, is: $N_2=84.3\%$; $CO_2=8.44\%$; $CO=1.29\%$.

At the end of the reaction, after 33 hours altogether, acetone (350 ml) is added to the liquid left in the reaction flask (138.1 g), the precipitate is recovered by filtration and recrystallized from acetone obtaining N,N'-bis-(2-hydroxyethyl)-piperazine (35.1 g, 0.202 mol) with a yield, calculated on the starting diethanolamine, of 28.2%.

EXAMPLE 4

N,N'-tetra-(2-hydroxyethyl)oxamide (2.64 g, 0.01 mol) and diethanolamine (2.10 g, 0.02 mol) are charged in a reaction flask equipped as described in Example 1 and the reaction mixture is heated to 210° C. for 20 hours. Acetone (15 ml) is then added and the precipitate is recovered by filtration and recrystallized from acetone. N,N'-bis-(2-hydroxyethyl)-piperazine (0.7 g) is thus obtained with a yield on N,N'-tetra(2-hydroxyethyl)oxamide of 40.2%, calculated on the starting diethanolamine.

We claim:

1. A process for preparing N,N'-bis-(2-hydroxyethyl)-piperazine (I)

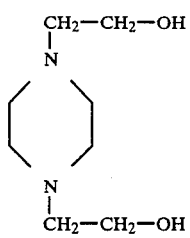

which comprises heating to a temperature of from 50° to 268° C. oxamide (II)

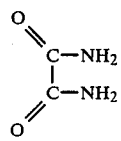

with diethanolamine (III)

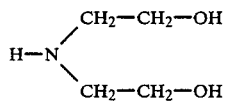

wherein the molar ratio diethanolamine/oxamide is >2, the reaction being carried out under conditions wherein the molar ratio of diethanolamine (III) to oxamide (II) is initially at least 2, and the total amount of diethanolamine (III) employed during the course of the reaction is such that the ratio of the total amount of diethanolamine (III) employed to oxamide (II) during the course of the reaction is greater than 2, any unreacted diethanolamine (III) serving as a reaction solvent.

2. The process of claim 1 wherein the molar ratio diethanolamine/oxamide is from 2.5 to 20.

3. The process of claim 2 wherein said ratio is from 3.5 to 10.

4. The process of claim 3 wherein said ratio is about 4.

5. The process of claim 1 wherein the reaction is carried out in a single step, by heating the mixture of oxamide and diethanolamine to a temperature of from 130° to 268° C.

6. The process of claim 5 wherein said temperature is from 160° to 220° C.

7. The process of claim 1, wherein the reaction is carried out in two separate steps by in a first step, heating a mixture of oxamide and an at least double molar amount of diethanolamine to a temperature of from 50° to 160° C. until NH₃ evolution subsides and in a second step, raising then the temperature to a value of from 160° to 268° C.

8. The process of claim 7 wherein an additional amount of diethanolamine is added at the end of the first step.

9. A process for preparing N,N'-bis-(2-hydroxyethyl)-piperazine (I)

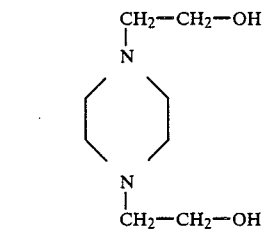

which comprises heating to a temperature of from 160° to 268° C. N,N'-tetra-(2-hydroxyethyl)oxamide (IV)

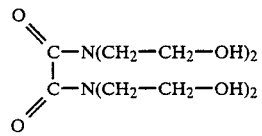

in the presence of diethanolamine.

10. The process of claim 9 wherein the reaction is carried out in the presence of at least an equimolar amount of diethanolamine with respect to the starting compound of formula (IV).

* * * * *